| United States Patent [19] | [11] Patent Number: 4,684,719 |
|---|---|
| Nishikawa et al. | [45] Date of Patent: Aug. 4, 1987 |

[54] α,α-TREHALOSE FATTY ACID DIESTER DERIVATIVE

[75] Inventors: Yoshihiro Nishikawa; Kimihiro Kanemitsu, both of Kanazawa; Tatsuhiko Katori, Ibaragi; Akihiro Shibata, Narashino; Kenichi Kukita, Kashiwa, all of Japan

[73] Assignee: SS Pharmaceutical Co., Ltd., Tokyo, Japan

[21] Appl. No.: 734,198

[22] Filed: May 15, 1985

[30] Foreign Application Priority Data

Jun. 5, 1984 [JP] Japan ................................. 59-115204

[51] Int. Cl.$^4$ ........................................... C07H 13/02
[52] U.S. Cl. .................... 536/119; 536/115; 536/120
[58] Field of Search ................... 514/53; 536/115, 119, 536/120

[56] References Cited

U.S. PATENT DOCUMENTS 4,491,659  1/1985  Durette ................................. 536/4.1

FOREIGN PATENT DOCUMENTS 0200311  12/1982  Japan ...................................... 514/53

OTHER PUBLICATIONS

March, *Advanced Organic Chemistry*; Reactions, Mechanisms, and Structure, 1968, p. 319.

*Primary Examiner*—Johnnie R. Brown
*Assistant Examiner*—Elli Peselev
*Attorney, Agent, or Firm*—Oblon, Fisher, Spivak, McClelland & Maier

[57] ABSTRACT

Disclosed herein are novel α,α-trehalose fatty acid diester derivatives useful as carcinostatic substances and surface-activating materials and represented by the general formula (I):

wherein $R^1$ means an alkyl group having 1-21 carbon atoms, $R^2$ denotes a hydrogen atom or carbobenzoxy group, and $R^3$ stands for a hydrogen atom or benzyl group. Their preparation processes are also disclosed.

1 Claim, No Drawings

α,α-TREHALOSE FATTY ACID DIESTER DERIVATIVE

BACKGROUND OF THE INVENTION

This invention relates to α,α-trehalose fatty acid diester derivatives and their preparation processes.

SUMMARY OF THE INVENTION

The present inventors have proceeded with the synthesis of a variety of fatty acid esters of trehalose and the investigation on various activities thereof, and have found that α,α-trehalose fatty acid diester derivatives represented by the following general formula (I):

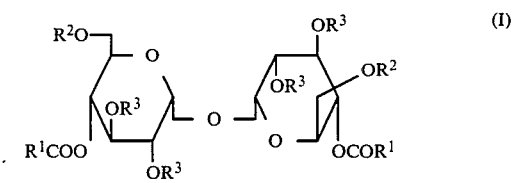

wherein $R^1$ means an alkyl group having 1–21 carbon atoms, $R^2$ denotes a hydrogen atom or benzyloxycarbonyl group and $R^3$ stands for a hydrogen atom or benzyl group have carcinostatic activities besides their surface-activating effects and these compounds have low toxicity, resulting in completion of the present invention.

Therefore, the present invention provides the novel α,α-trehalose fatty acid diester derivatives useful as carcinostatic substances and surface-activating materials and represented by the formula (I) and their preparation processes.

DETAILED DESCRIPTION OF THE INVENTION

The α,α-trehalose fatty acid diester derivatives of this invention may be classified into compounds of the following two groups (Ia) and (Ib):

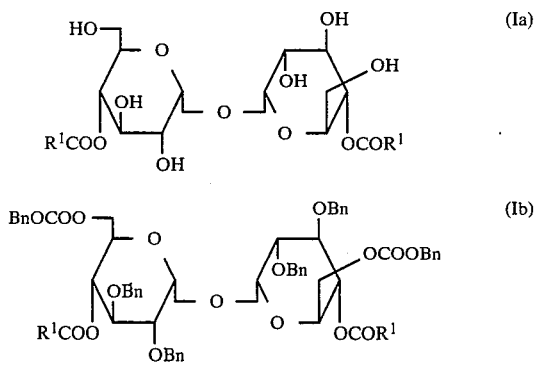

wherein Bn means a benzyl group and $R_1$ has the same meaning as defined above. These compounds may be prepared for example by the following processes.

Process 1

Carbobenzoxy chloride (V) is caused to act in the presence of a base on 2,3,2′,3′-tetra-O-benzyl-α,α-trehalose (IV) to obtain 2,3,2′,3′-tetra-O-benzyl-6,6′-di-O-carbobenzoxy-α,α-trehalose (II), on which the acylating agent (III) is additionally caused to act in the presence of a base.

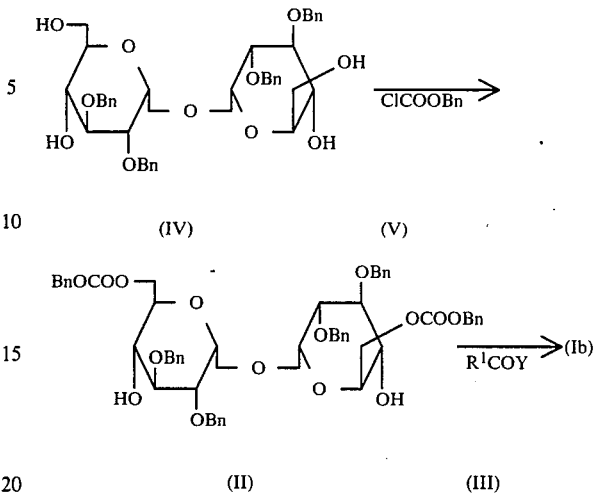

wherein Y means a halogen atom or $R^1COO$ group and $R^1$ and Bn have the same meaning as defined above.

Process 2

The 2,3,2′,3′-Tetra-O-benzyl-6,6′-di-O-carbobenzoxy-α,α-trehalose-4,4′-fatty acid diester (Ib) is dissolved in an organic solvent, followed by its hydrogenolysis using a reducing catalyst.

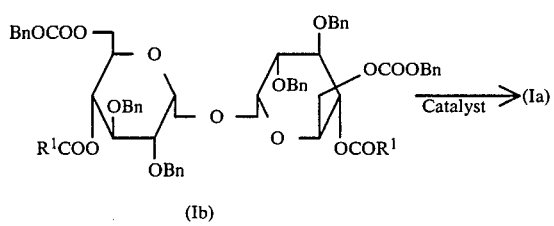

wherein $R^1$ and Bn have the same meaning.

In the reactions of Process 1, the first step is completed by using the compound (V) in an amount of 2–4 moles based on the compound (IV) and then reacting them in the presence of a base, at −30° C.—room temperature and for 3–24 hours.

The starting material, namely, the compound represented by the formula (IV) is a known compound and is obtained in three steps from α,α-trehalose. As the base useful in this reaction, may be mentioned an organic base such as pyridine, 4-dimethylaminopyridine or triethylamine or an inorganic base such as sodium hydroxide, potassium hydroxide, sodium carbonate, potassium carbonate or sodium hydrogencarbonate. As the solvent, a halogenated hydrocarbon such as chloroform or methylene chloride is preferred. It may however be possible to employ an organic base per se as the solvent where the organic base is as the base.

The thus-obtained reaction mixture is poured into ice water and then extracted with an organic solvent such as chloroform. After distilling off the solvent under reduced pressure, the reaction product is purified by silica gel chromatography and then recrystallized from a suitable solvent, thereby obtaining the compound (II) in a pure state.

The reaction of the second step can be completed by using the compound (III) in an amount of 2–6 moles per mole of the compound (II) and reacting them in the presence of a base, at 0° C.—room temperature and for 10–70 hours. As the base and solvent, it is possible to use the same base and solvent as those employed in the first step. Accordingly, the compound (Ib) may be obtained directly by causing the compound (III) to react further on the compound (II) without isolating the compound (II) from the compound (IV).

The compound (Ib) can be obtained in a pure form when the thus-obtained reaction mixture is poured into ice water and extracted with an organic solvent such as chloroform, and after distilling off the solvent under reduced pressure, the compound (Ib) is purified by silica gel chromatography.

The reaction of Process 2 can be brought to completion by using a catalyst in an amount of 0.05–1 part by weight per part by weight of the compound (Ib) obtained in Process 1 and catalytically reducing the compound (Ib) at room temperature to 70° C. for 1–10 hours.

As solvents useful in the above reaction, may be mentioned alcohols such as methanol, ethanol, propanol and isopropanol; halogenated hydrocarbons such as chloroform and methylene chloride; and their mixed solvents. On the other hand, conventionally-known catalytically-reducing catalysts such as palladium-carbon, palladium black and Raney nickel may each be used as the catalyst.

Since the compound (Ib) is converted almost stoichiometrically to the intended compound (Ia) in the above reaction, the compound (Ia) can be easily obtained in a pure form by filtering off the catalyst after completion of the reaction, concentrating the resultant filtrate and then recrystallizing the residue from a suitable solvent, for example, methanol, ethanol, ether, chloroform or the like.

Certain pharmacological activities were tested on the compound (I) of this invention. Results will hereinafter be described.

Pharmacological effects (1) Activities against Ehrlich carcinoma:

To 8 ICR female mice as a group, Ehrlich carcinoma cells were intraperitoneally implanted in an amount of $10^5$ cells per mouse. From an elapsed time of 24 hours after the implantation, the compound (I) of this invention which was suspended in physiological saline containing 0.5% of CMC-Na was intraperitoneally administered in predetermined dosages (0.4 mg/kg, 4.0 mg/kg and 40.0 mg/kg), once a day and for 10 days.

Upon an elapsed time of 30 days after the implantation of the carcinoma, the survival time of each mouse was counted. The average survival time of Control Group (C) and that of Group (T), in which the compound of this invention was administered, were obtained respectively. Antitumor effect (T/C %) was then determined in accordance with the following equation.

Antitumor effect $(T/C \%) = \dfrac{\text{Average survival time of Group } (T) \text{ administered with invention compound}}{\text{Average survival time of control Group } (C)} \times 100$ Results are given in Table 1.

TABLE 1

| Compound No. | Dosage (mg/kg) | Antitumor effect (T/C %) |
|---|---|---|
| 11 | 0.4 | 154 |
|  | 4.0 | 105 |
|  | 40.0 | 114 |
| 12 | 0.4 | 141 |
|  | 4.0 | 142 |
|  | 40.0 | 114 |
| 13 | 0.4 | 127 |
|  | 4.0 | 120 |
|  | 40.0 | 103 |
| 14 | 0.4 | 136 |
|  | 4.0 | 117 |
|  | 40.0 | 183 |
| 15 | 0.4 | 121 |
|  | 4.0 | 152 |
|  | 40.0 | 188 |
| 16 | 0.4 | 102 |
|  | 4.0 | 180 |
|  | 40.0 | 225 |
| 17 | 0.4 | 98 |
|  | 4.0 | 203 |
|  | 40.0 | 203 |
| 18 | 0.4 | 125 |
|  | 4.0 | 216 |
|  | 40.0 | 189 |
| 19 | 0.4 | 98 |
|  | 4.0 | 183 |
|  | 40.0 | 198 |
| 20 | 0.4 | 165 |
|  | 4.0 | 179 |
|  | 40.0 | 157 |
| Control | — | 100 |

(2) Cell-killing activities:

Leukemia L-5178Y cells were provided to a concentration of $2 \times 10^5$ cells/ml in PRMI 1640 culture medium which contained 10% of bovine fetus albumin. To portions of the above-prepared culture medium, the compound of this invention was added to concentrations 3.125, 6.25, 12.5, 25, 50, 100 and 300 μg/ml respectively. After culturing them for 48 hours in a 5% $CO_2$ incubator of 37° C., the numbers of live cells on respective portions of the culture were counted microscopically. Percentage proliferation was determined relative to Control and 50% Inhibitory Concentration ($IC_{50}$) was obtained by the probit diagram method. Results are shown in Table 2.

TABLE 2

| Compound No. | $IC_{50}$ (μg/ml) |
|---|---|
| 13 | >300 |
| 14 | 35.1 |
| 15 | 11.2 |
| 16 | 8.4 |
| 17 | 12.6 |
| 18 | >300 |

As has been described above, the compounds of this invention have carcinostatic activities besides surface-activating effects, and are safe compounds since they are saccharide derivatives. Accordingly, the compounds (I) of this invention are useful as carcinostatic agents and surfactants and also as intermediate raw materials therefor.

The invention will hereinafter be described by the following Examples.

EXAMPLE 1

Dissolved in 20 ml of pyridine and 20 ml of methylene chloride was 2.808 g of 2,3,2',3'-tetra-O-benzyl-α,α-trehalose (IV), followed by a dropwise addition of 2.046 g of carbobenzoxy chloride at 0° C. with stirring. Thereafter, the mixture was stirred overnight at room temperature. The reaction mixture was poured into ice water and then extracted with chloroform. The chloroform layer was washed with water and then dried over anhydrous sodium sulfate. After distilling off the solvent, the residue was purified by Florisil column chromatography which used benzenemethylene chloride as a developer. Upon recrystallization from ether-hexane, 2.80 g of 2,3,2′,3′-tetra-O-benzyl-6,6′-di-O-carbobenzoxy-α,α-trehalose (II) was obtained as colorless needle-like crystals (yield: 72%).

IR$\nu_{max}^{KBr}$: 3500,1725.

NMR δppm (CDCl$_3$): 2.1–2.7(br. s. 2H), 3.1–4.4(m. 12H),
4.56(s. 4H), 4.78(AB-type 4H),
4.98(s. 4H), 5.06(d. 2H),
7.1–7.5(m. 30H).

EXAMPLE 2

Dissolved in 30 ml of pyridine was 1.94 g of 2,3,2′,3′-tetra-O-benzyl-6,6′-di-O-carbobenzoxy-α,α-trehalose (II), followed by a dropwise addition of 1.82 g of stearoyl chloride at 0° C. with stirring. The resultant mixture was stirred at room temperature for 40 hours. The reaction mixture was poured into ice water and then extracted with chloroform. The chloroform layer was washed with water and then dried over anhydrous sodium sulfate. The solvent was distilled off. Upon purification by silica gel column chromatography which used hexane-ether as a developer, 2.70 g of 2,3,2′,3′-tetra-O-benzyl-6,6′-di-O-carbobenzoxy-4,4′-di-O-stearoyl-α,α-trehalose (Compound No. 9) was obtained in the form of colorless wax (yield: 90%).

EXAMPLE 3

Suspended in 60 ml of methylene chloride was 4.217 g of 2,3,2′,3′-tetra-O-benzyl-α,α-trehalose (IV), followed by an addition of 1.424 g of pyridine. While cooling the resultant mixture at −15° C., 3.071 g of carbobenzoxy chloride was added dropwise. After the dropwise addition, the temperature of the mixture was raised gradually to 0° C., at which it was stirred for 4 hours. Thereafter, 1.424 g of pyridine was added, followed by a further addition of 3.433 g of decanoyl chloride. The resultant mixture was then stirred at room temperature for 17 hours, and the resultant reaction mixture was poured into ice water and then extracted with chloroform. The chloroform layer was washed successively with water, 2N hydrochloric acid and water, and thereafter dried over anhydrous sodium sulfate. The solvent was distilled off. Upon purification by silica gel chromatography which used hexane-ethyl acetate as a developer, 5.05 g of 2,3,2′,3′-tetra-O-benzyl-6,6′-di-O-carbobenzoxy-4,4′-di-O-decanoyl-α,α-trehalose (Compound No. 5) was obtained in the form of colorless syrup (yield: 66%).

EXAMPLE 4

Dissolved in 40 ml of chloroform and 20 ml of methanol was 2.40 g of 2,3,2′,3′-tetra-O-benzyl-6,6′-di-O-carbobenzoxy-4,4′-di-O-stearoyl-α,α-trehalose (Compound No. 9). Using 0.70 g of palladium black as a catalyst, the resultant mixture was stirred at room temperature for 4 hours while introducing hydrogen gas. The catalyst and resulting crystal deposit were collected by filtration, followed by their washing with hot chloroform-methanol. The filtrate was concentrated under reduced pressure and recrystallized from chloroform-methanol, thereby obtaining 0.90 g of 4,4′-di-O-stearoyl-α,α-trehalose (Compound No. 19) as colorless scale-like crystals (yield: 93%).

EXAMPLE 5

In the same manner as in Examples 2, 3 and 4, the compounds given in Tables 3 and 4 were synthesized. The compounds obtained in Examples 2, 3 and 4 are also shown in the tables.

TABLE 3

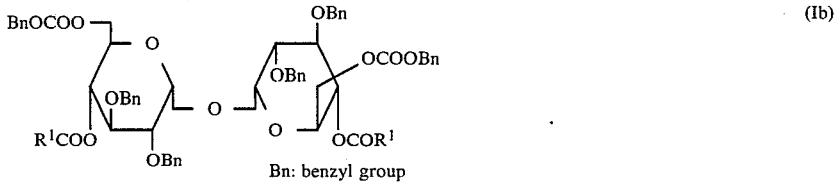

Bn: benzyl group

| Comp'd No. | −R$^1$ | Appearance | Optical rotation [α]$_D^{21}$ (C = 1.00, chloroform) | IR $\nu_{max}^{film}$ cm$^{-1}$ | NMR (δppm in CDCl$_3$) |
|---|---|---|---|---|---|
| 1 | −CH$_3$ | Colorless syrup | +68.8° | 3050, 2965, 1745 | 7.5–7.1(m. 30H), 5.06(s. 4H), 4.77(AB-type 4H), 4.64 (s. 4H), 5.16(d. 2H), 4.5–3.4(m. 12H), 1.94(s. 6H) |
| 2 | −(CH$_2$)$_2$CH$_3$ | Colorless syrup | +67.6° | 3045, 2950, 1750 | 7.5–7.1(m. 30H), 5.05(s. 4H), 4.75(AB-type 4H), 4.64 (s. 4H), 5.16(d. 2H), 4.5–3.4(m. 12H), 2.18(t. 4H), 1.57(q. t. 4H), 0.91(t. 6H) |
| 3 | −(CH$_2$)$_4$CH$_3$ | Colorless syrup | +61.4° | 3050, 2950, 1750 | 7.5–7.1(m. 30H), 5.08(s. 4H), 4.79(AB-type 4H), 4.66(s. 4H), 5.18(d. 2H), 4.4–3.4(m. 12H), 2.21(t. 4H), 1.9–1.1(m. 12H), 0.88(t. 6H) |
| 4 | −(CH$_2$)$_6$CH$_3$ | Colorless syrup | +56.3° | 3045, 2940, 1750 | 7.5–7.1(m. 30H), 5.08(s. 4H), 4.78(AB-type 4H), 4.67(s. 4H), 5.19(d. 2H), 4.4–3.4(m. 12H), 2.21(t. 4H), 1.26(m. 20H), 0.88(t. 6H) |
| 5 | −(CH$_2$)$_8$CH$_3$ | Colorless syrup | +57.7° | 3045, 2945, 1755 | 7.5–7.1(m. 30H), 5.10(s. 4H), 4.80(AB-type 4H), 4.68(s. 4H), 5.19(d. 2H), 4.4–3.4(m. 12H), 2.22(t. 4H), 1.24(m. 28H), 0.88(t. 6H) |
| 6 | −(CH$_2$)$_{10}$CH$_3$ | Colorless syrup | +57.4° | 3045, 2940, 1750 | 7.5–7.1(m. 30H), 5.07(s. 4H), 4.76(AB-type 4H), 4.65(s. 4H), 5.17(d. 2H), 4.4–3.4(m. 12H), 2.21(t. 4H), 1.23(m. 36H), 0.88(t. 6H) |
| 7 | −(CH$_2$)$_{12}$CH$_3$ | Colorless syrup | +59.3° | 3040, 2940, 1750 | 7.5–7.1(m. 30H), 5.08(s. 4H), 4.78(AB-type 4H), 4.66(s. 4H), 5.18(d. 2H), 4.4–3.4(m. 12H), 2.21(t. 4H), 1.23(m. 44H), 0.88(t. 6H) |
| 8 | −(CH$_2$)$_{14}$CH$_3$ | Colorless syrup | +50.5° | 3045, 2940, 1750 | 7.5–7.1(m, 30H), 5.06(s. 4H), 4.76(AB-type 4H), 4.64(s. 4H), 5.16(s. 2H), 4.4–3.4(m. 12H), 2.22(t, 4H), |

TABLE 3-continued (Ib)

[Structure shown with BnOCOO, OBn, OBn, OBn, OBn, OBn, OCOOBn, R¹COO, OCOR¹ groups; Bn: benzyl group]

| Comp'd No. | $-R^1$ | Appearance | Optical rotation $[\alpha]_D^{21}$ (C = 1.00, chloroform) | IR $\nu_{max}^{film}$ cm$^{-1}$ | NMR ($\delta$ppm in CDCl$_3$) |
|---|---|---|---|---|---|
| 9 | $-(CH_2)_{16}CH_3$ | Colorless wax | +54.7° | 3045, 2940, 1745 | 1.23(m. 52H), 0.88(t. 6H) 7.5–7.1(m. 30H), 5.08(s. 4H), 4.78(AB-type 4H), 4.66(s. 4H), 5.18(d. 2H), 4.4–3.4(m. 12H), 2.20(t. 4H), 1.23(m. 60H), 0.88(t. 6H) |
| 10 | $-(CH_2)_{20}CH_3$ | Colorless syrup | +43.9° | 3050, 2950, 1755 | 7.5–7.1(m. 30H), 5.08(s. 4H), 4.77(AB-type 4H), 4.65(s. 4H), 5.18(d. 2H), 4.4–3.4(m. 12H), 2.21(t. 4H), 1.26(m. 76H), 0.88(t. 6H) |

TABLE 4

(Ia)

[Structure shown with HO, OH, OH, OH, OH, OH, R'COO, OCOR' groups]

| Comp'd No. | $-R^1$ | Appearance m.p. (°C.) | Optical rotation $[\alpha]_D^{21}$ (C = 1.00, pyridine) | IR $\nu_{max}^{KBr}$ cm$^{-1}$ | NMR ($\delta$ppm in d$_5$-pyridine) |
|---|---|---|---|---|---|
| 11 | $-CH_3$ | Colorless glass-like crystals 87–97 | +160.7° | 3400, 2960, 1732 | 7.3–6.0(br. s. 6H), 5.9–5.3(m. 4H), 5.1–4.4(m. 4H), 4.4–3.9(m. 6H) 1.94(s. 6H) |
| 12 | $-(CH_2)_2CH_3$ | Colorless plate-like crystals 146–150 | +151.6° | 3400, 2960, 1745 | 7.6–5.3(br. 6H), 5.9–5.3(m. 4H), 5.1–4.4(m. 4H), 4.4–3.9(m. 6H), 2.22(t. 4H), 1.56(q. t. 4H), 0.82(t. 6H) |
| 13 | $-(CH_2)_4CH_3$ | Colorless plate-like crystals 173–175 | +145.0° | 3400, 2960, 1745 | 7.4–6.1(br. 6H), 5.9–5.4(m. 4H), 5.1–4.4(m. 4H), 4.4–3.9(m. 6H), 2.26(t. 4H), 1.1–0.9(m. 12H), 0.76(t. 6H) |
| 14 | $-(CH_2)_6CH_3$ | Colorless plate-like crystals 169–172 | +131.2° | 3400, 2950, 1745 | 7.5–5.2(br. 6H), 6.0–5.2(m. 4H), 5.1–4.4(m. 4H), 4.4–3.9(m. 6H), 2.30(t. 4H), 1.19(m. 20H), 0.83(t. 6H) |
| 15 | $-(CH_2)_8CH_3$ | Colorless leaf-like crystals 183–184 | +119.0° | 3400, 2945, 1745 | 7.6–5.2(br. 6H), 5.9–5.2(m. 4H), 5.0–4.4(m. 4H), 4.4–3.9(m. 6H), 2.28(t. 4H), 1.16(m. 28H), 0.84(t. 6H) |
| 16 | $-(CH_2)_{10}CH_3$ | Colorless leaf-like crystals 171–173 181–183 | +110.3° | 3400, 2940, 1748 | 7.3–5.6(br. 6H), 5.8–5.2(m. 4H), 5.0–4.4(m. 4H), 4.3–3.9(m. 6H), 2.27(t. 4H), 1.18(m. 36H), 0.85(t. 6H) |
| 17 | $-(CH_2)_{12}CH_3$ | Colorless leaf-like crystals 156–159 179–183 | +103.2° | 3400, 2940, 1748 | 6.27(br. s. 6H), 5.8–5.2(m. 4H), 5.0–4.4(m. 4H), 4.3–3.9(m. 6H), 2.28(t. 4H), 1.23(m. 44H), 0.87(t. 6H) |
| 18 | $-(CH_2)_{14}CH_3$ | Colorless scale-like crystals 106–110 184–190 | +94.8° | 3400, 2940, 1748 | 6.21(br. s. 6H), 5.8–5.2(m. 4H), 5.0–4.4(m. 4H), 4.3–3.9(m. 6H), 2.26(t. 4H), 1.22(m. 52H), 0.86(t. 6H) |
| 19 | $-(CH_2)_{16}CH_3$ | Colorless scale-like crystals 106–109 185–189 | +91.5° | 3400, 2935, 1755 | 7.2–5.1(br. 6H), 5.8–5.2(m. 4H), 4.9–4.3(m. 4H), 4.2–3.8(m. 6H), 2.5–2.0(t. 4H), 1.26(m. 60H), 0.88(t. 6H) |
| 20 | $-(CH_2)_{20}CH_3$ | Colorless scale-like crystals 101–106 140–146 | +82.6° | 3400, 2930, 1738 | 6.20(br. s. 6H), 5.8–5.2(m. 4H), 5.0–4.3(m. 4H), 4.3–3.8(m. 6H), 2.5–2.0(t. 4H), 1.28(m. 76H), 0.88(t. 6H) |

What is claimed is:

1. An α,α-trehalose fatty acid diester derivative represented by the formula (I):

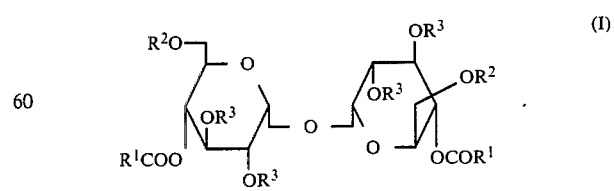

(I)

wherein $R^1$ means an alkyl group having 1–21 carbons atoms, $R^2$ denotes a hydrogen atom or carbobenzoxy group, and $R^3$ stands for a hydrogen atom or benzyl group.

* * * * *